(12) United States Patent
Kuhn et al.

(10) Patent No.: US 12,179,179 B2
(45) Date of Patent: Dec. 31, 2024

(54) CATALYST FOR SYNGAS CONVERSION TO LIGHT OLEFINS

(71) Applicant: University of South Florida, Tampa, FL (US)

(72) Inventors: John Kuhn, Wesley Chapel, FL (US); Babu Joseph, Tampa, FL (US); Yang He, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 17/691,082

(22) Filed: Mar. 9, 2022

(65) Prior Publication Data

US 2022/0288570 A1    Sep. 15, 2022

Related U.S. Application Data

(60) Provisional application No. 63/200,481, filed on Mar. 10, 2021.

(51) Int. Cl.
| | |
|---|---|
| *B01J 21/04* | (2006.01) |
| *B01J 23/825* | (2006.01) |
| *B01J 37/18* | (2006.01) |
| *C07C 1/04* | (2006.01) |

(52) U.S. Cl.
CPC ............ *B01J 23/825* (2013.01); *B01J 21/04* (2013.01); *B01J 37/18* (2013.01); *C07C 1/041* (2013.01); *C07C 1/044* (2013.01); *C07C 1/0445* (2013.01); *C07C 1/048* (2013.01); *C07C 2521/04* (2013.01); *C07C 2523/825* (2013.01)

(58) Field of Classification Search
CPC ........................................................ B01J 21/04
See application file for complete search history.

(56) References Cited

U.S. PATENT DOCUMENTS

| | | | |
|---|---|---|---|
| 9,126,876 B2 * | 9/2015 | de Jong | ................ C07C 1/044 |
| 2011/0105630 A1 | 5/2011 | Dorner et al. | |
| 2017/0015554 A1 | 1/2017 | Siengchum et al. | |

(Continued)

FOREIGN PATENT DOCUMENTS

| | | | | |
|---|---|---|---|---|
| CA | 2919752 C | * | 10/2023 | ............ B01J 21/02 |
| CN | 106607037 A | * | 5/2017 | |
| IN | 201711038824 | | 11/2017 | |

(Continued)

OTHER PUBLICATIONS

Hexana, et al. "Indium as a chemical promoter in Fe-based Fischer-Tropsch synthesis." Applied Catalysis A: General 377.1-2 (2010): 150-157.

(Continued)

*Primary Examiner* — Jun Li
(74) *Attorney, Agent, or Firm* — Quarles & Brady LLP

(57) ABSTRACT

The present disclosure provides a composition. In an embodiment, a catalyst composition is provided and includes from 85 mol % to 95 mol % iron metal, and from 15 mol % to 5 mol % indium metal, wherein mol % is based on total moles of iron metal and indium metal. Also provided is a process of contacting, under reaction conditions, a gaseous mixture of carbon monoxide, hydrogen and optionally water with the catalyst composition. The process includes forming a reaction product composed of light olefins.

16 Claims, 13 Drawing Sheets

(56) References Cited

U.S. PATENT DOCUMENTS

2020/0047159 A1* 2/2020 Xiao .................. B01J 35/23
2021/0178368 A1 6/2021 Gascon et al.

FOREIGN PATENT DOCUMENTS

| | | | |
|---|---|---|---|
| IN | 202017052543 A | 2/2021 | |
| IN | 201711015470 | 5/2021 | |
| JP | 2021532984 A * | 12/2021 | |
| WO | 20200176210 A1 | 9/2020 | |
| WO | WO-2020205494 A1 * | 10/2020 | ............ B01J 21/005 |

OTHER PUBLICATIONS

Su, et al. Syngas to light olefins conversion with high olefin/paraffin ratio using ZnCrOx/AlPO-18 bifunctional catalysts. Nat Commun 10, 1297 (2019). 1-8.

* cited by examiner

FIG. 5B
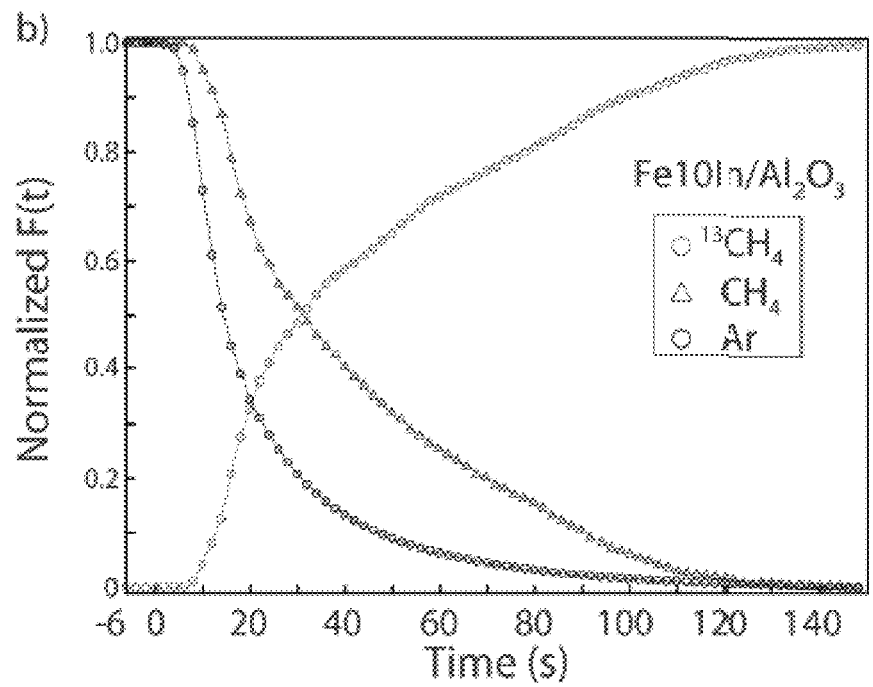
FIG. 6A
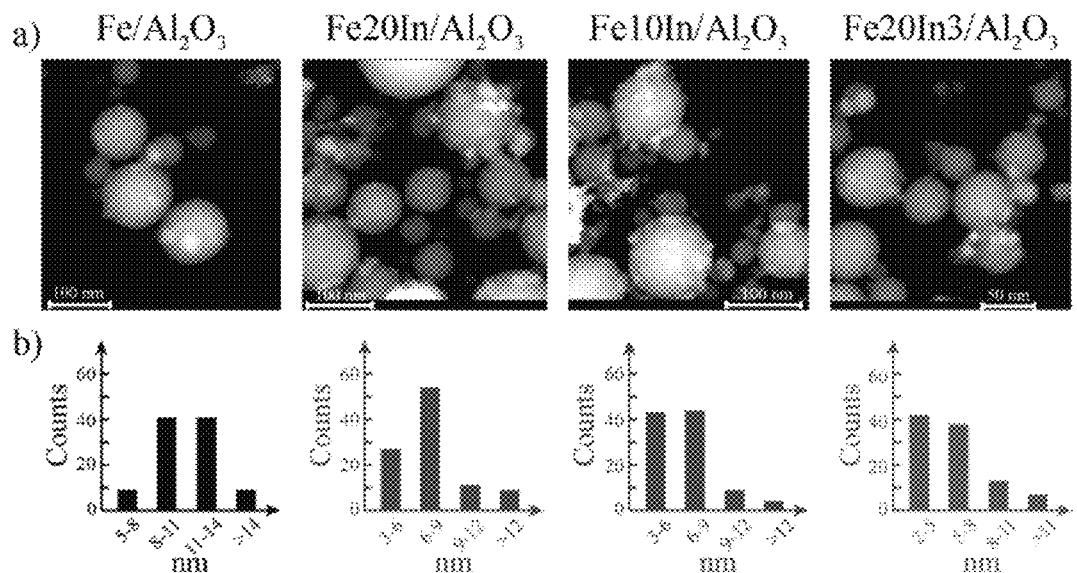
FIG. 6B

CATALYST FOR SYNGAS CONVERSION TO LIGHT OLEFINS

CROSS-REFERENCE TO RELATED APPLICATIONS

This application claims the benefit of priority of U.S. Provisional Patent Application No. 63/200,481, filed on Mar. 10, 2021, the entirety of which is herein incorporated by reference.

STATEMENT REGARDING FEDERALLY SPONSORED RESEARCH

This invention was made with government support under Grant Number DEEE8008488 awarded by the U.S. Department of Energy. The government has certain rights in the invention.

BACKGROUND

Light olefins, that is, $C_2=C_4$-olefins are critical feedstocks to produce a wide range of chemicals, such as polymers, drugs, and solvents. Traditionally, light olefins are predominantly produced by high-temperature catalytic cracking of large alkanes and dehydrogenation of light alkanes in natural gas. Due to the depletion of oil reserves, it is of importance to develop alternative technologies for light olefin production. This has attracted a lot of attention in transforming $C_1$ compounds (e.g., $CH_4$, $CH_3OH$, and CO) into olefins via a C—C coupling reaction path. Fischer-Tropsch synthesis (FTS) is an effective process to produce light olefins by using synthesis gas (syngas).

Extensive efforts have been made to develop selective heterogeneous catalysts for FTS to olefins and various promoted and unpromoted metal-based (e.g., Fe-, Co-, and Ru-based) catalysts have been studied. However, these materials exhibited low olefin selectivity, high methane formation, and large $CO_2$ emission especially at an elevated temperature. These materials lacked control over surface chemistry, which led to over-hydrogenation and C—C/C=C bond-breaking reactions. Recently, some composite materials composed of a zeolite and Zr- or Zn-based binary oxide were discovered that showed selectivity toward olefins with low $CH_4$ production. However, these materials require an aggressive pressure (e.g., 25 bars) to keep the high catalytic activity and selectivity. These materials also suffer from high selectivity toward $CO_2$ (>40%).

Precise control of surface carbon and hydrogen affinities is needed to promote C—C coupling while inhibiting over-hydrogenation and methane formation in transforming syngas to light olefins. It is also equally critical to control the activation of CO on the catalyst surface to limit the production of $CO_2$. The post-transition-metal elements (e.g., Ga, In, Sn, and Tl) have been shown to have the capability to inhibit unselective over-hydrogenation reactions when incorporated with metals in various alkane dehydrogenation reactions.

SUMMARY

The present disclosure is directed to a catalyst composition and the process of utilizing the catalyst composition in FTS. The present process decreases the gap of operating conditions between methane reforming and FTS, which can be upgraded to achieve valuable olefins by combining these two reactions in an intensified process. In an embodiment, the present disclosure is directed to an alumina-supported In-promoted Fe catalyst (with Fe/In loading ratios of 20:1, 10:1, and 20:3) that was investigated in the reaction. Pure Fe metal on alumina was also studied as a comparison. Bounded by no particular theory, it is believed that introduction of In element into Fe catalysts can modify the amount of surface Fe sites and surface Fe electronic structure, which allows control of the surface chemistry in the reaction. Applicant unexpectedly discovered that the ensemble size of Fe sites, the catalyst surface reactivity, and the surface Fe electronic structure can be systematically modified as a function of Fe:In loading ratios. These novel findings are supported by performance studies, CO TPD studies, SSITKA, and XPS analysis.

The present disclosure provides a composition. In an embodiment, a catalyst composition is provided and includes from 85 mol % to 95 mol % iron metal, and from 15 mol % to 5 mol % indium metal, wherein mol % is based on total moles of iron metal and indium metal.

The present disclosure provides a process. In an embodiment, the process includes contacting, under reaction conditions, a gaseous mixture of carbon monoxide, hydrogen and optionally water with a catalyst composition. The catalyst composition includes from 85 mol % to 95 mol % iron metal, and from 15 mol % to 5 mol % indium metal, wherein mol % is based on total moles of iron metal and indium metal. The process includes forming a reaction product composed of light olefins.

BRIEF DESCRIPTION OF THE DRAWINGS

FIG. 3A) $CH_4$ selectivity, FIG. 3B) $C_2$-$C_4$ alkane and olefin selectivity, FIG. 3C) $C_5$+ hydrocarbon selectivity, and FIG. 3D) $CO_2$ selectivity. CO conversion was kept in a range of 8-10% by varying catalyst loading. Reaction condition: 400° C., 5 bars, and 2:1 $H_2$:CO ratio.

FIGS. 5A and 5B show normalized transient curves from a CO/$H_2$/He/Ar to $^{13}$CO/Hz/He over alumina supported (FIG. 5A) Fe and (FIG. 5B) Fe10In under a CO methanation reaction condition: 400° C., 10:1 $H_2$:CO, and 1.85 bars.

FIGS. 6A and 6B are respective dark-field TEM images and particle size distributions of the as-prepared alumina supported Fe and Fe—In catalysts with Fe:In loading ratios of 20:1, 10:1, and 20:3.

DEFINITIONS

Figure 1A:
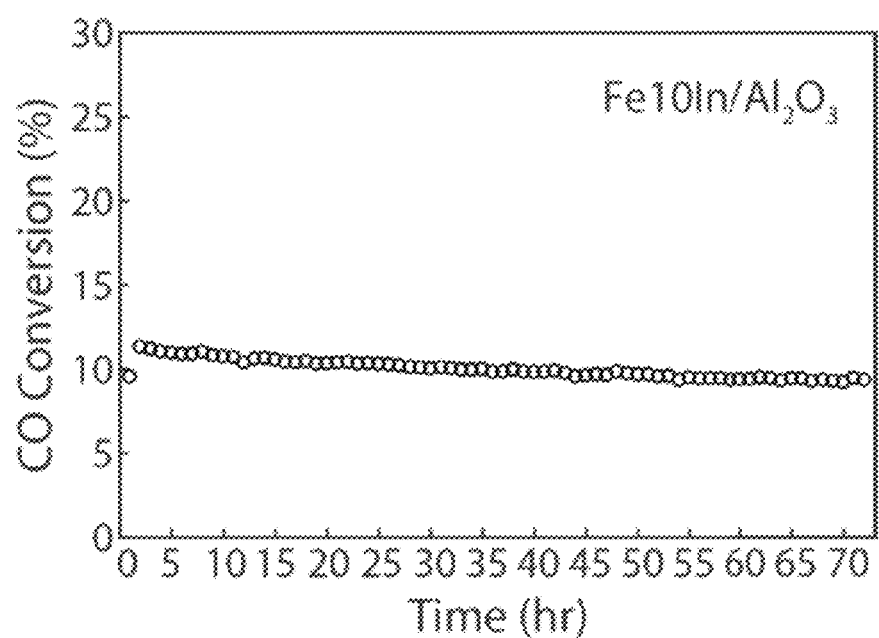
FIG. 1A is a graph showing the conversion of CO over 72 hours under reaction conditions for $Al_2O_3$ supported Fe10In catalyst, in accordance with an embodiment of the present disclosure.

The numerical ranges disclosed herein include all values from, and including, the lower and upper value. For ranges containing explicit values (e.g., from 1 or 2, or 3 to 5, or 6, or 7), any subrange between any two explicit values is included (e.g., the range 1-7 above includes subranges of from 1 to 2; from 2 to 6; from 5 to 7; from 3 to 7; from 5 to 6; etc.).

A "catalyst" refers to a material active in a chemical reaction. For example catalyst includes a material active in a Fischer-Tropsch synthesis reaction.

The term "composition" refers to a mixture of materials which comprise the composition, as well as reaction products and decomposition products formed from the materials of the composition.

The terms "comprising," "including," "having" and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term "consisting essentially of" excludes from the scope of any succeeding recitation any other component, step, or procedure, excepting those that are not essential to operability. The term "consisting of" excludes any component, step, or procedure not specifically delineated or listed. The term "or," unless stated otherwise, refers to the listed members individually as well as in any combination.

The term "contacting" refers to the act of touching, making contact, bringing into immediate proximity in order to bring about a chemical reaction.

The term "conversion" refers to the degree to which a given reactant in a particular reaction (e.g., dehydrogenation, hydrogenation, etc.) is converted to products. Thus 100% conversion of carbon monoxide means complete consumption of carbon monoxide, and 0% conversion of carbon monoxide means no measurable reaction of carbon monoxide.

"Fisher-Tropsch synthesis" ("FTS") refers to a chemical reaction that converts a mixture of carbon monoxide (CO) and hydrogen ($H_2$), among other potential components such as $CO_2$, into a mixture of hydrocarbons and water often in the presence of a catalyst.

"Incipient wetness impregnation" (or "IWI") is a technique for the synthesis of heterogeneous catalysts. MI typically includes dissolving an active metal precursor in an aqueous solution or an organic solution. The metal-containing solution is added subsequently to a catalyst support containing the same pore volume as the volume of solution that was added. Capillary action draws the solution into the pores. The catalyst can then be dried and/or calcined to drive off the volatile components within the solution, depositing the metal on the catalyst surface.

"Light olefin" is a $C_2$ to $C_4$ α-olefin and includes ethylene ($C_2$), propylene ($C_3$), and butene ($C_4$), interchangeably referred to as "$C_2$=$C_4$ olefin."

An "olefin" is an unsaturated, aliphatic hydrocarbon having a carbon-carbon double bond.

The term "selectivity" refers to the degree to which a particular reaction forms a specific product, rather than another product. For example, for the conversion of syngas, 50% selectivity for $C_2$-$C_4$ olefins refers to 50% of the reaction products formed are $C_2$-$C_4$ olefins, and 100% selectivity for $C_2$-$C_4$ olefins indicates that 100% of the reaction products formed are $C_2$-$C_4$ olefins. The selectivity is based on the reaction product formed, regardless of the conversion of the particular reaction. The selectivity for a given product produced from a given reactant can be defined as weight percent (wt %) of that product relative to the total weight of the products formed from the given reactant in the reaction.

The term "syngas," as used herein, relates to a gaseous mixture composed of hydrogen ($H_2$) and carbon monoxide (CO), and optionally water and optionally $CO_2$. The syngas, which is used as a feed stream, may optionally include up to 10 mol % of other components such as $CO_2$ and lower hydrocarbons (lower HC), depending on the source and the intended conversion processes. The other components may be side-products or unconverted products obtained in the process used for producing the syngas. The syngas may contain such a low amount of molecular oxygen ($O_2$) so that the quantity of $O_2$ present does not interfere with the Fischer-Tropsch synthesis reactions and/or other conversion reactions. For example, the syngas may include not more than 1 mol % $O_2$, not more than 0.5 mol % $O_2$, or not more than 0.4 mol % $O_2$. The syngas may have a hydrogen ($H_2$) to carbon monoxide (CO) molar ratio of from 1:3 to 3:1. The partial pressures of $H_2$ and CO may be adjusted by introduction of inert gas to the reaction mixture.

Test Methods

CO Temperature-Programmed Desorption ("CO TPD"). CO TPD was performed using a MKS mass spectrometer (Cirrus LM-92). Before the TPD study, all catalysts were brought to the steady state analyzed by gas chromatography (GC) under the same reaction conditions (reaction temperature: 400° C., 5 bars pressure, $H_2$/CO/$N_2$ flow rate 56:28:16 ratio, 14.5 sccm). The pressure was then released and the inlet gases were switched to Ar with 50 sccm at 400° C. for 1 hour (h). After the degassing treatment, the reactor was cooled down to room temperature and 10% CO/Ar (50 sccm total flow rate) was introduced into the reactor for 0.5 h. The gas-phase CO was removed by flowing Ar until the CO signal was minimized and stabilized in the mass spectra. Temperature was then ramped up to 800° C. with a step of 10° C./min.

Powder X-ray Diffraction ("pXRD"). pXRD measurements were performed on a PANalytical X'Pert Pro system using Cu Kα radiation. The scan of XRD covered the 2θ range 10-90° with a step size of 0.017° at a scan speed of 0.006°/s.

Steady State Isotropic Transient Kinetic Analysis (SSITKA). The SSITKA setup consisted of two independent feed lines. The first one contained the regular CO, $H_2$, a diluted gas (He), and a tracer (Ar). The second line was dedicated to the isotopic CO, $H_2$, and a diluent (He). Two back pressure regulators (swagelok) were utilized to maintain the two feed lines under the same pressure. A two-position four-way Valco manual valve was used to perform the isotopic switches, and the outline stream from the reactor was monitored with a MKS mass spectrometer (Cirrus LM-92). To perform the SSITKA experiment, 100 mg of Fe/$Al_2O_3$ was mixed with 400 mg of SiC (~100 mesh) and loaded into a stainless-steel tube reactor with a diameter of 6 mm. In the case of Fe10In/$Al_2O_3$, 200 mg catalyst was applied to keep a similar CO conversion with the Fe/$Al_2O_3$ catalyst. Quartz wool was inserted into the top and bottom of the catalyst bed to minimize the dead space in the reactor. Before each experiment, the catalyst was reduced in situ under the conditions the same as those used for the performance tests. The FTS reaction (400° C., 5 bars) was then performed until it achieved the steady state. This aimed to make the catalyst have a similar surface to that observed in the performance test. Subsequently, the pressure was released and the reactor was cooled down to 100° C. At this temperature, the flow was changed to 1 sccm CO, 10 sccm $H_2$, 13.5 sccm He, and 0.5 sccm Ar and the pressure was increased up to 1.85 bars. The temperature was increased to 400° C., and the reaction was performed for 10 h before the SSITKA study. An online gas chromatograph (Buck 910) equipped with FID and TCD was connected to the system to analyze the effluent. After the methanation reaction reached the steady state, a switch was performed from $^{12}CO/H_2/Ar/He$ to $^{13}CO/H_2/He$. The average surface residence time ($\tau_{avg}$) was obtained by calculating the peak area between the normalized transient responses of the product, $F^{CH_4}(t)$, and that of the inert gas tracer, $F^{Ar}(t)$, which was shown using the equation below. Due to the overlap of CO and Ar signals, the chromatographic effect of CO was negligible in this study.

$$\tau_{avg}^{CH_4} = \int_0^\infty [F^{CH_4}(t) - F^{Ar}(t)] dt$$

Temperature-Programmed Reduction ("TPR"). The TPR study was performed using a quartz U-tube reactor (0.25 in. outer diameter). A MKS mass spectrometer (Cirrus LM-92) was employed to analyze the outlet gases. Approximately 80 mg sample was used in the TPR study. Degassing treatment was performed over the calcined catalyst at 150° C. with He (50 sccm) until the $H_2O$ signal reached close to 0. Then, $H_2$ was introduced with a $H_2$/He ratio of 1:9 and at a 50 sccm total flow rate. Temperature was increased to 800° C. at a ramping rate of 10° C./min.

Transmission electron microscopy and energy dispersive spectroscopy ("TEM and EDS"). Dark-field TEM was utilized to measure the particle distribution and particle size of Fe/$Al_2O_3$ and In promoted Fe/$Al_2O_3$ catalysts with different Fe/In loadings before and after the reaction. The measurements were performed on a FEI Tecnai F30 operating at 200 kV. Holey carbon TEM grids were used for all measurements. All catalysts were dispersed in methanol and sonicated before loading on the TEM grids. STEM HAADF and EDS measurements over Fe10In/$Al_2O_3$ before and after the reaction were performed on a Tabs FEI F200I operating at 200 kV.

X-ray Photoelectron Spectroscopy ("XPS"). The chemical bonding states of Fe/$Al_2O_3$ and In-promoted Fe/$Al_2O_3$ catalysts before and after the reaction were analyzed using a Physical Electronics 5400 ESCA X-ray photoelectron spectrometer with a non-monochromatized Mg Kα X-ray excitation source of energy 1486.74 eV. A Voigt profile was used to fit the XPS data. The Fe 2p, In 3d, and C 1s spectra were collected over all catalysts. The binding energy of the C 1s peak at 284.6 eV was used as the reference.

DETAILED DESCRIPTION

The present disclosure provides a composition. In an embodiment, a catalyst composition is provided and includes from 85 mol % to 95 mol % iron (Fe) metal and from 15 mol % to 5 mol % indium (In) metal, wherein mol % is based on total moles of iron metal and indium metal. The catalyst composition includes from 85 mol %, or 90 mol %, or 95 mol % iron and respective 15 mol %, or 10 mol %, or 5 mol % indium.

In an embodiment, the catalyst composition in its pre-reaction state, is void of, or otherwise excludes nitrogen (or nitrides), and/or carbon (or carbides), or excludes both nitrogen (nitrides) and/or carbon (or carbides).

In an embodiment, the catalyst composition includes a support component. In a further embodiment, the support component is alumina ($Al_2O_3$).

In an embodiment, the catalyst composition includes alumina as the support component. The catalyst composition is void of nitrogen (nitrides) and/or carbon (carbides). The catalyst composition includes from 85 mol %, or 90 mol %, or 95 mol % iron and respective 15 mol %, or 10 mol %, or 5 mol % indium, wherein mol % is based on total moles of iron metal and indium metal. The catalyst composition further includes from 9.7 wt % to 9.9 wt % iron metal;
from 1 wt % to 3 wt % indium metal; and
from 87.3 wt % to 88.2 wt % alumina. Weight percent is based on total weight of the catalyst composition.

In an embodiment, the catalyst composition includes 95 mol % iron metal and 5 mol % indium metal based on the total moles of iron and indium. The catalyst composition also includes 9.9 wt % iron, 1 wt % indium, and 89.1 wt % alumina. The catalyst composition is void of nitrogen (nitrides) and/or carbon (carbides). Weight percent is based on total weight of the catalyst composition.

In an embodiment, the catalyst composition includes 90 mol % iron metal and 10 mol % indium metal based on the total moles of iron and indium. The catalyst composition also includes 9.8 wt % iron, 2 wt % indium, and 88.2 wt % alumina. The catalyst composition is void of nitrogen (nitrides) and/or carbon (carbides). Weight percent is based on total weight of the catalyst composition.

In an embodiment, the catalyst composition includes 85 mol % iron metal and 15 mol % indium metal based on the total moles of iron and indium. The catalyst composition also includes 9.7 wt % iron, 3 wt % indium, and 87.3 wt % alumina. The catalyst composition is void of nitrogen (nitrides) and/or carbon (carbides). Weight percent is based on total weight of the catalyst composition.

In an embodiment, the catalyst composition is placed under reaction conditions. The term "reaction conditions" includes a tubular reactor at a temperature from 150° C. to 450° C., or from 200° C. to 400° C., or from 300° C. to 400° C., and a pressure from 1 bar to 6 bar, or from 2 bar to 5 bar. The catalyst composition can be any catalyst composition as previously disclosed herein and includes from 85 mol % to 95 mol % iron metal and from 15 mol % to 5 mol % indium metal, where mol % is based on total moles of iron metal and indium metal; the catalyst composition also including alumina support component, or from 87.3 wt % to 89.1 wt % alumina (based on total weight of the catalyst composition). The catalyst composition under reaction conditions is contacted with a gaseous mixture of carbon monoxide, hydrogen, and optional water and the catalyst composition has
- (i) from 40% to 60%, or from 40% to 50% light olefin selectivity, and/or
- (ii) less than or equal to 20% $CO_2$ selectivity, or from 1% to 17% $CO_2$ selectivity, and/or
- (iii) less than or equal to 25 wt % methane selectivity, or from 1% to 23% methane selectivity.

The present disclosure provides a process. In an embodiment, the process includes contacting, under reaction conditions, a gaseous mixture composed of carbon monoxide, hydrogen and optionally water with a catalyst composition. The catalyst composition includes from 80 mol % to 95 mol % iron metal, and from 20 mol % to 5 mol % indium metal, wherein mol % is based on the total moles of iron metal and indium metal in the catalyst composition. The process includes forming a reaction product composed of light olefins.

The reaction conditions include a tubular reactor at a temperature from 150° C. to 450° C., or from 200° C. to 400° C., or from 300° C. to 400° C., and a pressure from 1 bar to 6 bar, or from 2 bar to 5 bar. The catalyst composition is placed into the tubular reactor, the tubular reactor subsequently configured to the reaction conditions. The gaseous mixture composed of carbon monoxide, hydrogen, and optionally water is introduced into, or otherwise flows through, the tubular reactor (at reaction conditions). In an embodiment, the gaseous mixture is a syngas. The gaseous mixture contacts the catalyst composition. By way of the contacting, the process forms a reaction product that contains light olefins.

The catalyst composition may be any catalyst composition as previous disclosed herein. In an embodiment, the catalyst composition includes alumina as the support component and the catalyst composition includes from 85 mol %, or 90 mol %, or 95 mol % iron and respective 15 mol %, or 10 mol %, or 5 mol % indium, wherein mol % is based on total moles of iron metal and indium metal. Prior to the contacting step, the catalyst composition is void of nitrogen (nitrides) and/or void of carbon (carbides). The catalyst composition further includes from 9.7 wt % to 9.9 wt % iron metal;
from 1 wt % to 3 wt % indium metal; and
from 87.3 wt % to 89.1 wt % alumina. Weight percent is based on total weight of the catalyst composition.

In an embodiment, the process includes exposing, before the contacting step with the syngas, the catalyst composition to a mixture of $H_2$-containing gas at a temperature from 300° C. to 500° C., or 400° C. to at least partially reduce the iron and the indium.

In an embodiment, the reaction conditions include the tubular reactor at a reaction temperature from 300° C. to 450° C., or 400° C., a pressure from 2 bar to 6 bar, or 5 bar, and the gaseous mixture has a $H_2$:CO ratio from 1:1-3:1. The process includes forming a reaction product composed of
- (i) from 40 wt % to 60 wt %, or from 40 wt % to 50 wt % light olefin, and/or
- (ii) less than or equal to 20 wt % $CO_2$, or from 1 wt % to 17 wt % $CO_2$, and/or
- (iii) less than or equal to 25 wt %, or from 1 wt % to 23 wt % methane.

By way of example, and not limitation, some embodiments of the present disclosure will now be described in the following examples.

EXAMPLES

Catalyst Synthesis.

$Al_2O_3$ (70% delta, 30% gamma phase, Alfa Aesar) supported Fe and a series of In-promoted Fe catalysts were synthesized using the incipient wetness impregnation method. $Fe(NO_3)_3 \cdot 9H_2O$ (Sigma-Aldrich) and $In(NO_3)_3 \cdot xH_2O$ (Alfa Aesar) were utilized as Fe and In sources. Both nitrate salts were first dissolved into a diluted nitric acid solution and then deposited onto the alumina support ($Al_2O_3$). The iron loading in this study was kept as 10 wt %. A series of In-promoted Fe (Fe/In molar ratios of 20:1, 10:1, and 20:3) were also produced. All samples were dried overnight at 120° C., followed by calcination at 400° C. for 5 hours (h) to remove nitrogen/nitrides and water. The catalyst inventive examples (IE) are provided in Table 1 below. Weight percent is based on total weight of the catalyst composition.

TABLE 1

| Inventive Example | Fe:In molar ratio | Iron load (wt %) | Indium load (wt %) | Alumina load (wt %) |
|---|---|---|---|---|
| Fe20In (IE1) | 20:1 | 9.9 | 1 | 89.1 |
| Fe10In (IE2) | 10:1 | 9.8 | 2 | 88.2 |
| Fe20In3 (IE3) | 20:3 | 9.7 | 3 | 87.3 |

Performance Tests.

A. Reduction. Before the catalytic performance test, in situ reduction was performed using 50% $H_2/N_2$ at 400° C. for 3 h. After that, a stainless-steel tubular reactor with a diameter of 6 mm was charged with hydrogen, carbon monoxide, and nitrogen with a 56:28:16 ratio (total flow rate:14.5 sccm). $N_2$ was used as an internal standard. The reaction temperature and pressure were kept at 400° C. and 5 bar, respectively. The reaction product was analyzed using an on-line gas chromatograph (Buck 910) equipped with a HayeSep-D column and a flame ionization detector (FID) and a thermal conductivity detector (TCD). To study the effect of the Fe/In loading on CO conversion, all catalysts were kept at the same loading (0.1 g). To compare product selectivity, the catalyst loading was varied to keep CO conversion in the range of 8-12%. All catalysts were mixed with 1.0 g 100-mesh SiC to minimize pressure drop and maintain a uniform bed.

B. Catalytic Performance

Figure 1B:
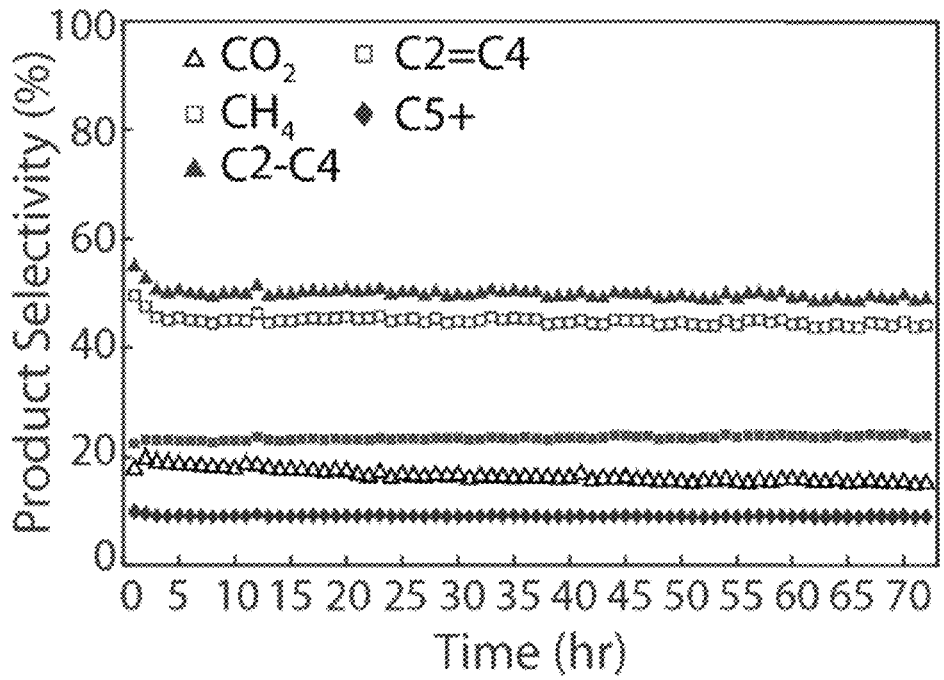
FIG. 1B is a graph showing catalytic activity, stability and selectivity of FTS for $Al_2O_3$ supported Fe10In catalyst, in accordance with an embodiment of the present disclosure.
Figure 1C:
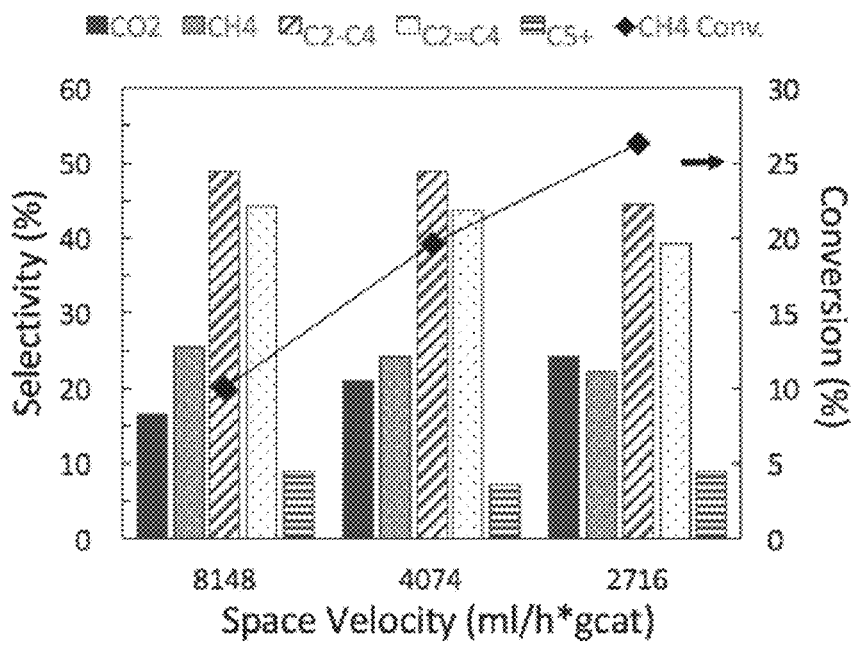
FIG. 1C is a graph showing the effect of space velocity on the catalyst performance.
Figure 1D:
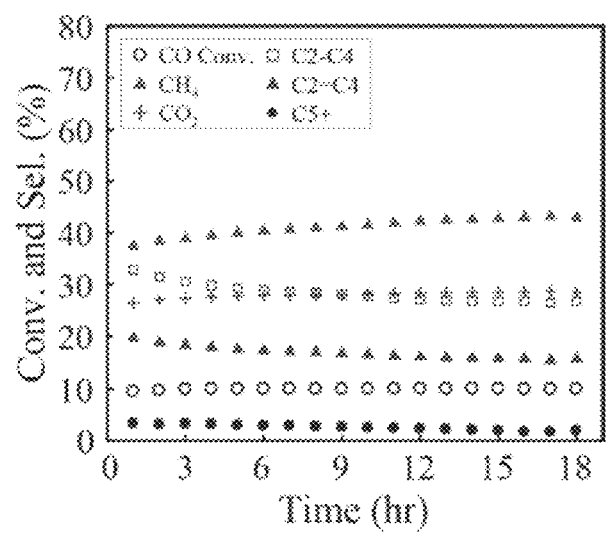
FIG. 1D is a graph showing FTS performance results over alumina supported Fe.
Figure 1E:
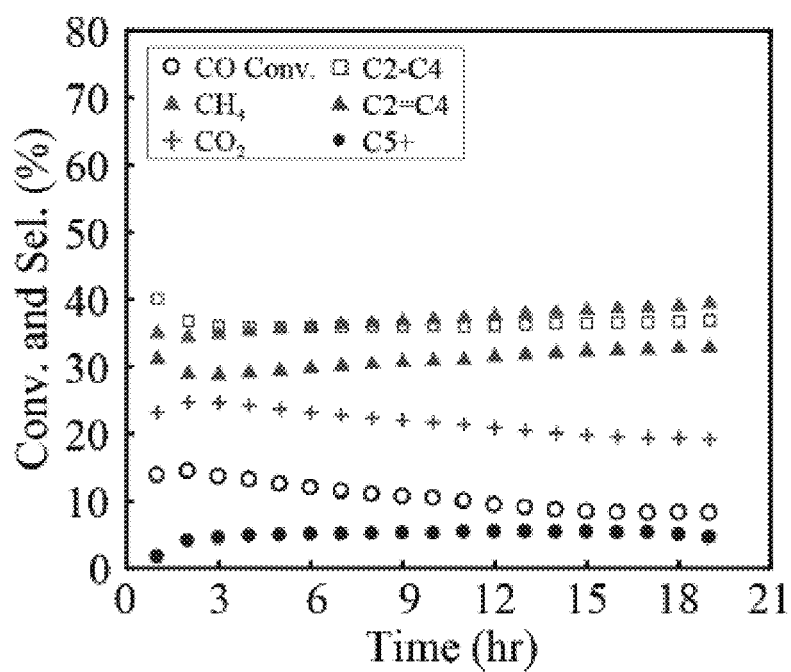
FIG. 1E is a graph showing FTS performance results over alumina supported Fe20In, in accordance with an embodiment of the present disclosure.
Figure 1F:
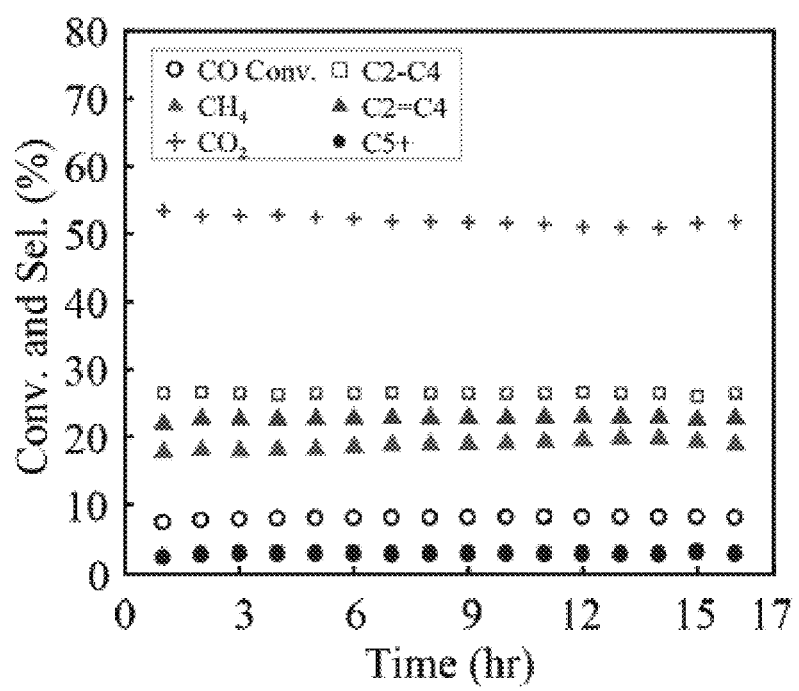
FIG. 1F is a graph showing FTS performance results over alumina supported Fe20In3, in accordance with an embodiment of the present disclosure.

Performance of catalyst IE2, Fe10In/$Al_2O_3$, exhibited stable performance (see FIGS. 1A-1C). The conversion of CO was stable dropping from 11% to 9% after extended operation of 72 hours under reaction conditions of $H_2/CO=2$, temperature 400° C., pressure 5 bar, and space velocity 7800 ml/h*gcat (FIG. 1A). It is noted that the selectivity of $CO_2$ was included when reporting product selectivity. The results showed excellent selectivity towards light olefins (40-60%, or 45%) with low $CO_2$ (16%) emission (FIG. 1B). Stability towards all products was appreciable with only minor deactivation (e.g. 1% for olefins) detected after 72 hours at the steady state.

Furthermore, space velocity and $H_2/CO$ ratio were also varied to investigate how they affected the catalytic performance of Fe10In/$Al_2O_3$ catalyst (IE2). The results showed that a higher space velocity could lower CO conversion and $CO_2$ formation with a minor effect on the product distribution of hydrocarbons (FIG. 1C).

Figure 3A:
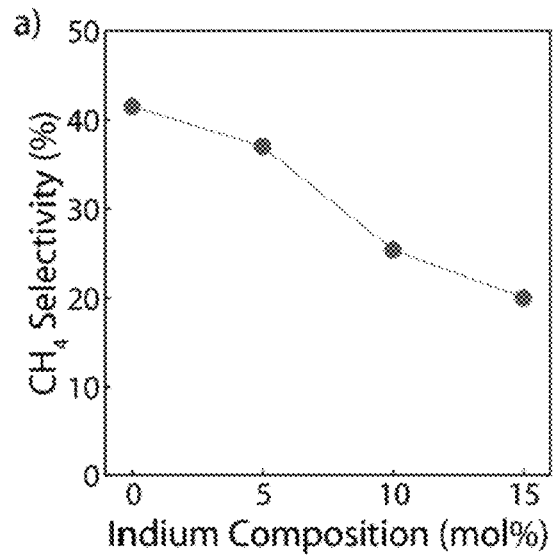
FIGS. 3A, 3B, 3C, and 3D are graphs showing catalytic performance of FTS over alumina supported Fe—In catalyst with different Fe:In loading ratios.

By way of comparison, recent published work about converting syngas to light olefins is summarized in Table 2, below. Bao and co-workers have shown that using a composite material consisting of SAPO-34, micro pore zeolite, and ZnCrOx could give a light olefin selectivity up to 80% in hydrocarbons (not including $CO_2$) with low $CH_4$ production at 400° C. and 25 bar. Other studies have reported light olefin selectivity in hydrocarbons from syngas, e.g., $MnO_2$/MSAPO-34, a modified zeolite, ZnCrOx/MOR, a mixed metal oxide supported on mordenite zeolite, and Zr/Zn/SSZ-13, a chabazite (CHA)-type aluminosilicate zeolite, at similar reaction conditions. However, the selectivity of $CO_2$ for the catalysts in these studies was reported to be greater than 40% on this type of catalyst even under a less harsh reaction condition (lower reaction temperature or higher pressure) when compared to inventive examples 1-3, which indicated a lack of control over $CO_2$ production. Promoted transition metal catalysts (i.e., FeBi, $Cr_2Zn$, CoMn) were also reported and they also suffered from high $CO_2$ production (see Table 2). When $CO_2$ was considered in the calculation of selectivity in those studies, the light olefin selectivity was between 40% and 50% (see Table 2).

in FIG. 3A. Our results showed that the selectivity of $CH_4$ had a similar trend as the conversion with respect to Fe:In loading ratios. The pure Fe catalyst displayed the maximum $CH_4$ selectivity among all four catalysts (41%). This might be caused by the unselective dehydrogenation of surface-bounded CHx groups or the cleavage of C—C/C═C bonds. However, the selectivity monotonically dropped as In composition increased (37% for Fe20In (IE1), 23% for Fe10In (IE2), and 20% for Fe20In3 (IE3)), which suggested that the unselective dehydrogenation and C—C/C═C bond cleavage reaction paths could be limited by incorporating In element into Fe catalyst.

Figure 3B:
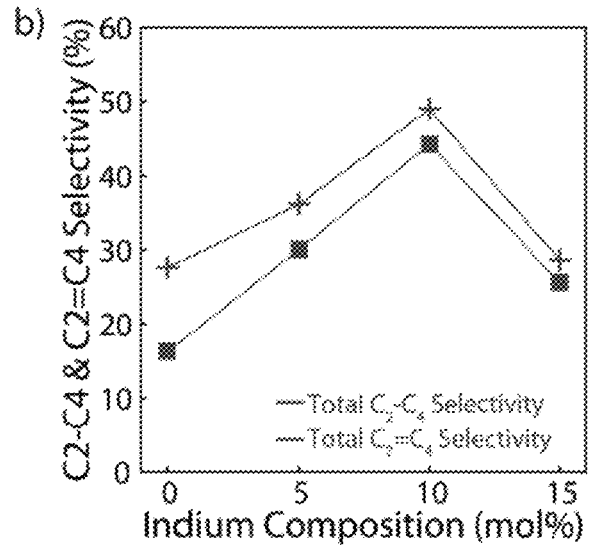

FIG. 3B displayed the correlation between the selectivity of $C_2$-$C_4$ hydrocarbons (total and olefins) and In composition in the catalysts. A volcano type of trend was found with the Fe10In (IE2) exhibited the highest selectivity towards both total hydrocarbons and olefins. The selectivity of $C_2$═$C_4$ olefins was measured as 16%, 30%, 44%, and 25% over pure Fe, Fe20In (IE1), Fe10In (IE2), and Fe20In3 (IE3), respectively. The total selectivity of $C_2$-$C_4$ hydrocar-

TABLE 2

| Catalyst | P (bar) and T (° C.) | $H_2$:CO | CO Conv. (%) | Olefin Sel. | $CO_2$ Sel. | $CH_4$ Sel. |
| --- | --- | --- | --- | --- | --- | --- |
| $MnO_x$-MSAPO (CS1) | 25 and 400 | 2.5:1 | 8.5 | 46.7 | 41.0 | 0.8 |
| ZrZn/SAPO-34 (CS2) | 10 and 400 | 2:1 | 9.5 | 34.6 | 45.0 | 3.3 |
| FeMnK@HM-S-1 (CS3) | 5 and 280 | 2:1 | 12 | ~40.0 | 29.4 | 12.0 |
| $ZnCrO_x$/MSAPO (CS4) | 25 and 400 | 2.5:1 | 17.0 | 44.0 | 45.0 | 1.1 |
| $Zn_{0.3}Ce_{1.0}Zr_{1.0}O_4$ (CS5) | 10 and 350 | 2:1 | 9.6 | 61.4 | 21.3 | 4.4 |
| $Cr_2Zn$ (CS6) | 20 and 400 | 2:1 | ~8 | ~32.0 | 40-50 | 8.0 |
| FeBi/$SiO_2$ (CS7) | 1 and 350 | 1:1 | 17 | 27.6 | 48.0 | 15.1 |
| CoMn (CS8) | 5 and 265 | 2:1 | 20.0 | 32.1 | 50.4 | 5.6 |
| Fe20In (IE1) | 5 and 400 | 2:1 | 38 | 30 | 20 | 38 |
| Fe10In (IE2) | 5 and 400 | 2:1 | 10 | 42 | 15 | 25 |
| Fe20In3 (IE3) | 5 and 400 | 2:1 | 3 | 28 | 49 | 20 |

CS-comparative sample

As shown in Table 2, inventive examples 1-3 displayed a comparable light olefin selectivity in comparison to comparative FTS composite materials (CS 1-8), with IE1-IE3 exhibiting better control of $CO_2$ production (IE 1-3 $CO_2$ selectivity less than or equal to 20%) at lower reaction pressure (IE 1-3 5 bar, compared to 25 bars for composite materials).

Figure 2:
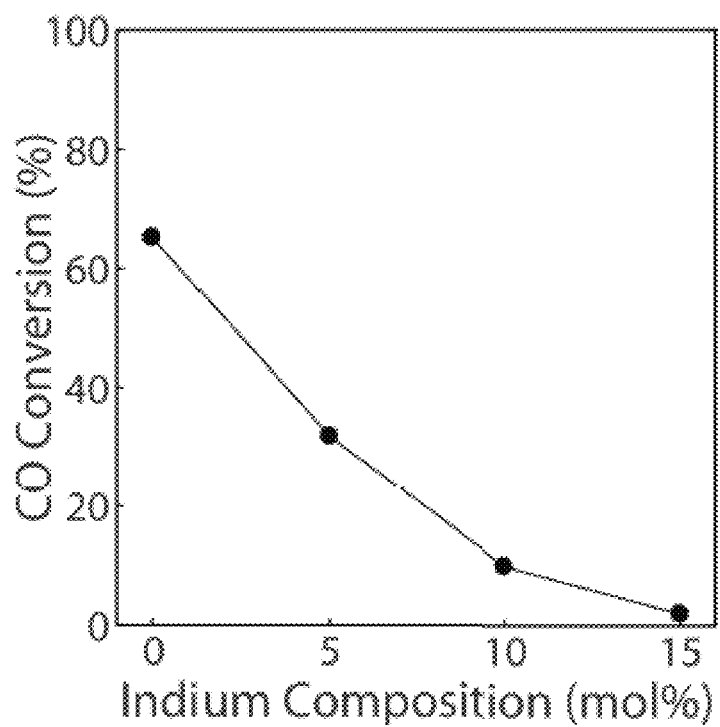
FIG. 2 is a graph showing CO conversion as a function of In composition in the catalysts. All catalysts were loaded with 100 mg. Temperature: 400° C., Pressure: 5 bars, GVSP: 7800 ml/h*gcat, and 2:1 $H_2$:CO ratio.

To understand how indium affects the surface chemistry of the $Al_2O_3$ supported In promoted Fe catalysts in FTS reaction, a systematic study was conducted using catalysts that consisted of (i) pure Fe, (ii) 5 mol % In-promoted Fe), (iii) 10 mol % In-promoted Fe, and (iv) 15 mol % In-promoted Fe. When studying the effect of In composition on CO conversion, all catalysts were kept at the same loading (0.1 g). The results showed a systematic and monotonic decrease in CO conversion as the In composition increased (see FIG. 2). In the case of pure Fe on $Al_2O_3$ support, CO conversion was 70%. The conversion decreased to 28% when 5 mol % In was introduced and further decreased to 10% and to 3% at 10 mol % and 15 mol % In loading, respectively. The trend indicated that the catalyst possessed a higher ability to activate CO without In incorporated. This ability appeared to be reduced when In was introduced, which could be attributed to the blocking of the surface reaction sites or an interaction between Fe and In.

Focusing on the selectivity, catalyst loadings were varied to keep a similar CO conversion (8-10%). All data reported in FIGS. 3A, 3B, 3C, and 3D were collected when the reaction achieved the steady state (see FIGS. 1A-1F). The correlation of $CH_4$ selectivity and In composition is reported bons also displayed a similar trend. The volcano trend clearly suggested that Fe10In catalyst (IE2) exhibited the most appropriate surface reactivity that can promote selective C—C coupling for light olefins while inhibiting unselective hydrogenation and C—C/C═C bond cleavage reactions.

The olefin to paraffin ratio (O/P ratio) was also calculated to estimate the degree of hydrogenation over all catalysts. The pure Fe catalyst exhibited the lowest O/P ratio, which could be ascribed to the over activation of C═C bond on the surface. This was supported by many experimental surface science studies on the adsorption of ethylene and butadiene where the enhanced surface carbon affinity of many transition metals (e.g. Ti, V, Mo, and W) can over activate the C═C bond, which led to complete decomposition and hydrogenation to form atomic carbon and alkanes. The O/P ratio significantly enhanced to 5.8, 9.4, and 8.5 over 5%, 10%, and 15% In-promoted Fe catalysts, respectively, which clearly showed the modifications on surface reactivity. These observations are in line with published work where the preservation of C═C bond could be promoted when incorporating the P-block or the post-transition-metal elements with the transition metals in a range of reactions. It is also noted that a drop of $C_2$-$C_4$/$C_2$═$C_4$ selectivity and O/P ratio was found over Fe20In3 (IE3) from Fe10In (IE2). This may be attributed to its reduced surface ensemble size, which will be discussed in the following paragraph.

Figure 3C:
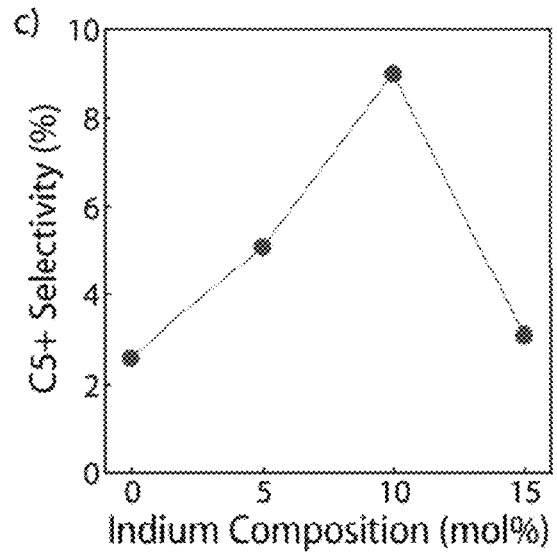

Beyond the light hydrocarbon products, the selectivity of liquid hydrocarbons ($C_5$+) was also reported with respect to In composition (see FIG. 3C). It is interesting to note that $C_5+$ selectivity also exhibited a volcano type of relationship with the In composition with Fe10In (IE2) possessing the highest selectivity, which is similar to the case of $C_2=C_4$ selectivity.

The results showed 3%, 5%, 9%, and 2% $C_5+$ selectivity over pure Fe, Fe20In (IE1), Fe10In (IE2), and Fe20In3 (IE3), respectively (FIG. 3C). The results again suggested that C—C coupling reaction could be promoted when In element was introduced. A drop in $C_5+$ selectivity was found over Fe20In3 (IE3), which might be caused by the reduced surface Fe-ensemble size because of In blocking. Focusing on the correlation of $CO_2$ selectivity and In composition, FIG. 3D showed an inverted-type volcano trend with the Fe10In catalyst (IE2) exhibited the lowest $CO_2$ emission.

Figure 3D:
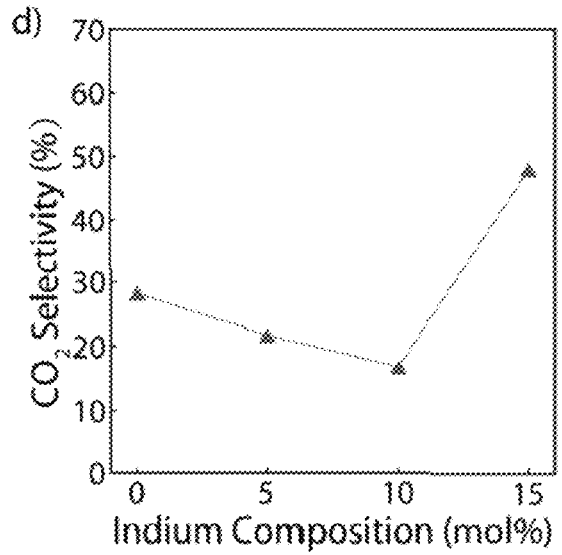

The $CO_2$ selectivity was measured as 28%, 22%, 16%, and 48% over Fe, Fe20In (IE1), Fe10In (IE2), and Fe20In3 (IE3), respectively (see FIG. 3D). The systematically decreased $CO_2$ selectivity from pure Fe to Fe10In (IE2) suggested that the degree of CO activation can be reduced by incorporating In into Fe. However, the increase of $CO_2$ selectivity over Fe20In3 (IE3) suggested that the water-gas shift reaction towards $CO_2$ production was promoted. It is worth noting the capability of controlling $CO_2$ selectivity over In-promoted Fe catalysts and that the Fe10In catalyst (IE2) exhibited a low $CO_2$ selectivity (Fe10In catalyst (IE2) 16% $CO_2$ selectivity, FIG. 3D).

Figure 4:
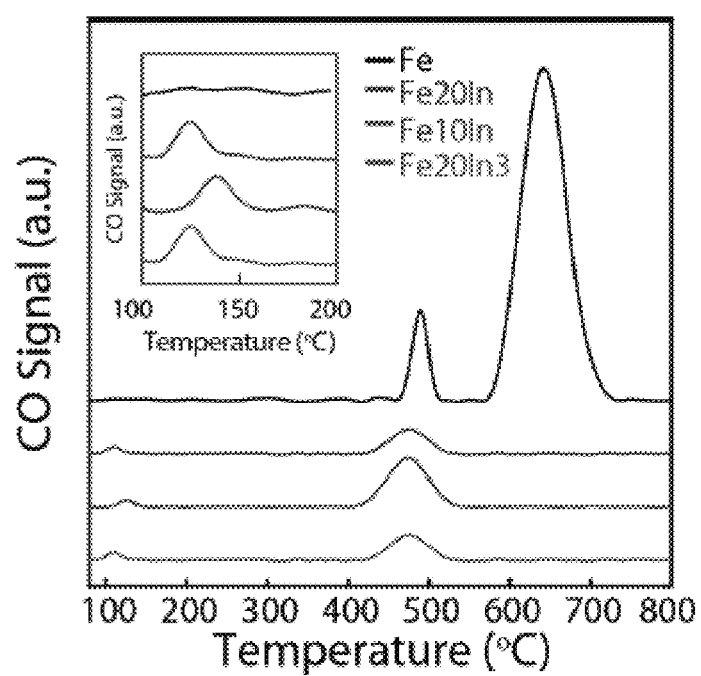
FIG. 4 is a graph showing a CO TPD study over alumina supported Fe and In-promoted Fe catalysts after the FTS reaction.

CO temperature programmed desorption (TPD) study was conducted over alumina supported Fe and Fe—In catalysts with 20:1, 10:1, and 20:3 Fe:In loading ratios to understand the effect of Fe:In composition change on the bonding strength of CO on the catalyst surface and how it affects catalytic reactivity. Performance details can be found in the method section. Briefly, all catalysts were first brought to steady state in FTS reaction and degassed at 400° C. under argon (Ar) for 1 hour (hr) before introducing CO. In the case of pure Fe catalyst, two major desorption peaks were found at 490° C. and 630° C. (see FIG. 4). The more pronounced peak at 630° C. suggested that the catalyst surface displayed plenty of highly reactive sites that led to a strong interaction with CO. However, the peak at 630° C. disappeared when In was introduced, which indicated that In blocked those reactive surface sites presented on Fe. The desorption peak at 490° C. over Fe was also shifted towards lower temperature over all three In-promoted Fe catalysts (475° C.). New desorption peaks at 100° C., 110° C., and 105° C. were found over Fe20In (IE1), Fe10In (IE2), and Fe20In3 (IE3), respectively (FIG. 4). These results suggested a decrease in surface reactivity towards CO when In was incorporated into Fe.

SSITKA study was conducted over Fe/$Al_2O_3$ and Fe10In/$Al_2O_3$ (IE2) catalysts to understand the effect of In on the promotion of C—C coupling to olefins and the inhibition of $CH_4$ formation. To facilitate the study, the study was performed under the methanation conditions ($H_2$/CO=10) to minimize the number of labeled products. An online GC was connected to the SSITKA apparatus to analyze the performance results. It was expected a big difference in the selectivity of $C_2$-$C_4$ hydrocarbons between using 2:1 and 10:1 $H_2$:CO ratios over these two catalysts. However, the same trend and the effect of In on catalytic performance still remained where the $CH_4$ formation was limited and the production of $C_2+$ hydrocarbons was promoted when In was incorporated into the Fe catalyst. Therefore, the understanding gained through our SSITKA study is applicable to the FTS reaction.

Figure 5A:
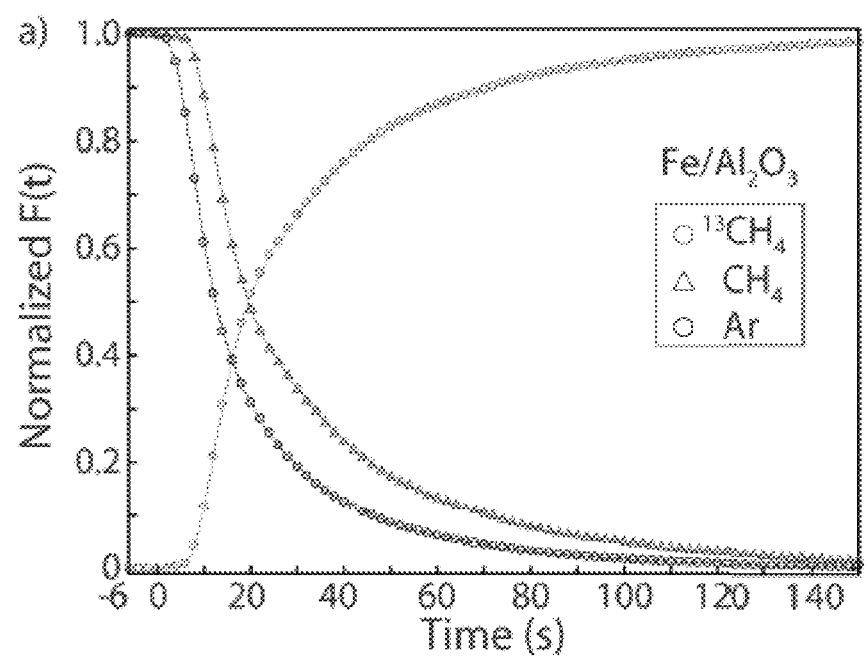

FIGS. 5A) and 5B) displayed the normalized transient curves from the CO/$H_2$/He/Ar to $^{13}$CO/$H_2$/He switch performed after 10 minutes of time on stream over Fe/$Al_2O_3$ and Fe10In/$Al_2O_3$ (IE2) catalysts. The surface residence time of $CH_4$ was calculated as 7.01 seconds (s) and 20.1 s for Fe/$Al_2O_3$ and Fe10In/$Al_2O_3$ (IE2), respectively. This result suggested that the adsorption of CHx species on the surface of Fe10In (IE2) was stronger than on Fe. The less stable CHx fragments on the Fe surface were likely due to the enhanced hydrogenation ability of the catalyst, which appeared to limit the C—C coupling reaction towards olefins. On the other hand, the more stable CHx intermediates on the Fe10In (IE2) surface appeared to favor the C—C coupling reaction path towards olefin production. The SSITKA study indicated that introducing In to the catalyst could stabilize the CHx fragments on the surface, which was critical to promote light olefin formation and inhibit the unselective hydrogenation to $CH_4$ in the FTS reaction.

Figure 6C:
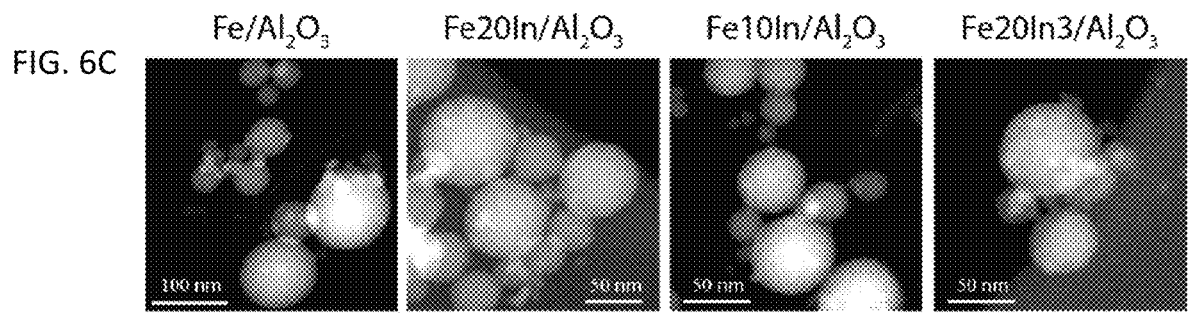
FIGS. 6C and 6D are respective dark-field TEM images and particle size distributions of the post-reaction alumina supported Fe and Fe—In catalysts with Fe:In loading ratios of 20:1, 10:1, and 20:3.
Figure 6D:
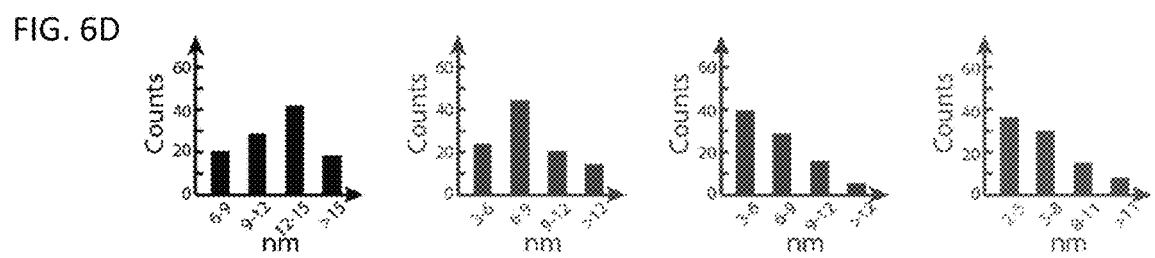

To shed light upon the essential features of alumina supported In-promoted Fe catalysts, multiple characterization techniques were employed. Dark-field TEM was employed to determine the particle size of the catalysts with different Fe:In loadings, shown in FIG. 6A. FIG. 6B showed the particle size distributions over Fe, Fe20In (IE1), Fe10In (IE2), and Fe20In3 (IE3) were 9.1, 7.1, 6.6, and 6.2 nm, respectively. The results suggested that introducing In into the catalyst seemed to promote the formation of smaller particles. This could be attributed to the inhibition of Fe sintering when In element was incorporated into the catalyst. After the FTS reaction (see FIG. 6C), only a slight particle size change was found over all materials (11.1, 8.7, 7.8, and 6.7 nm over Fe, Fe20In (IE1), Fe10In (IE2), and Fe20In3 (IE3), respectively, FIG. 6D). This suggested that all catalysts were quite stable under this reaction condition.

Figure 7:
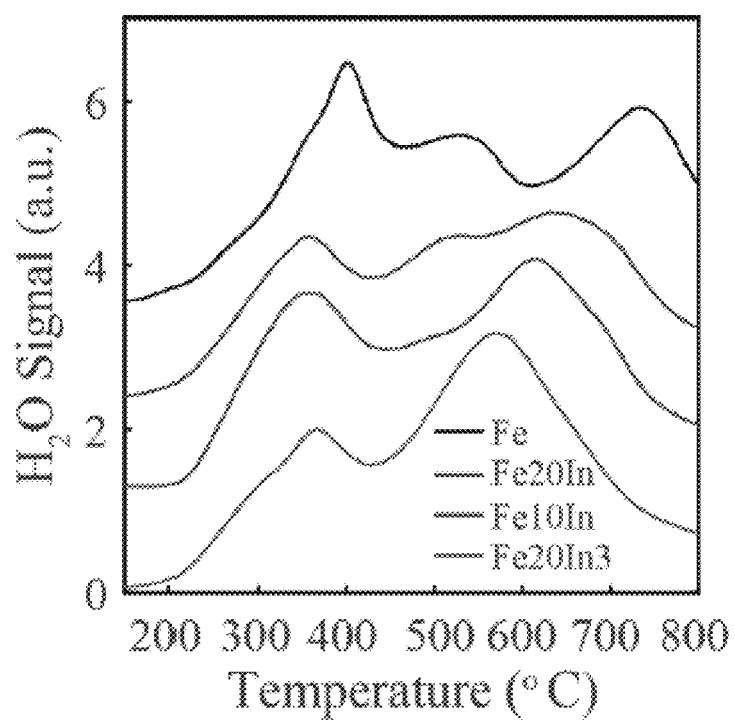
FIG. 7 is a graph showing a TPR study over a series of as-prepared supported Fe—In catalysts showing the catalyst reducibility is improved when In element is incorporated.
Figure 8A:
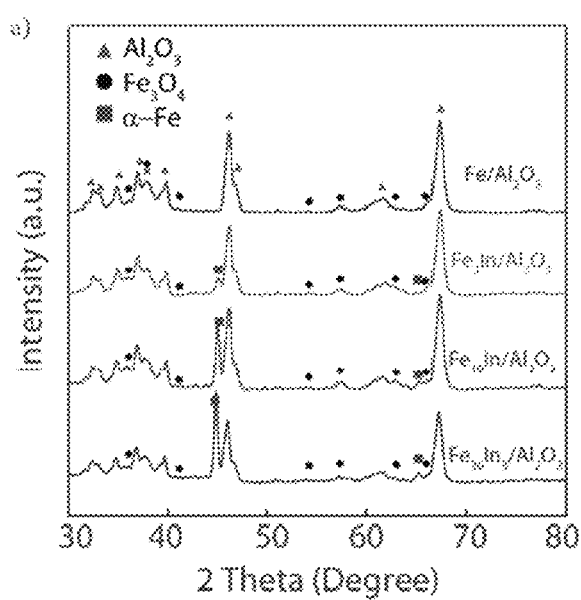
FIGS. 8A and 8B are graphs showing pXRD results FIG. 8A) as-prepared and FIG. 8B) post-reaction alumina Fe—In catalysts with different Fe:In loading ratios.
Figure 8B:
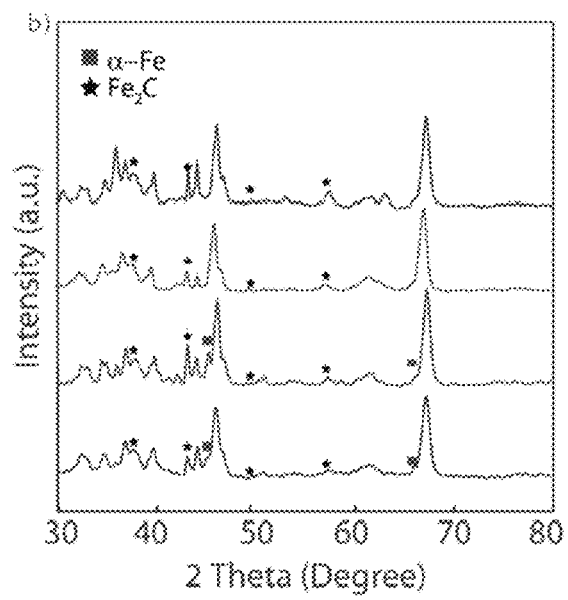

Temperature programmed reduction (TPR) studies were performed over pure Fe, Fe20In (IE1), Fe10In (IE2), and Fe20In3 (IE3) (see FIG. 7). The results showed that the incorporation of In element could promote catalyst reducibility and all the four catalysts could be finally reduced to metallic Fe at a temperature up to 800° C. pXRD measurements over the as-prepared catalysts showed that $Fe_3O_4$ was the major phase when Fe catalyst was not promoted with In. However, metallic Fe phase started to present and became more pronounced as In loading increased (see FIG. 8A). The results coincided with the TPR study where the reducibility of the catalyst can be promoted when more In was introduced into the catalyst. After reaction, the pXRD results indicated that $Fe_2C$ was the major carbide phase over Fe and Fe20In (IE1) whereas both $Fe_2C$ and $Fe_7C_3$ were found in the cases of Fe10In (IE2) and Fe20In3 (IE3) (see FIG. 8B).

Figure 9:
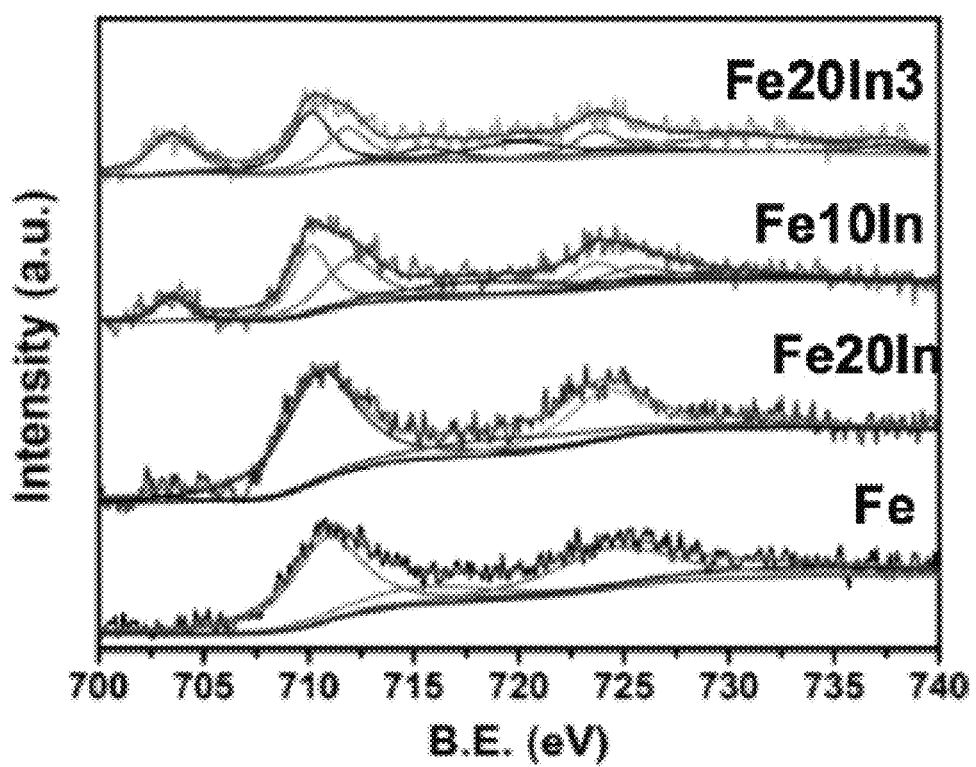
FIG. 9 is an XPS spectra of Fe 2p and In 3p1/2 over post-reaction Fe—In catalysts with various Fe:In loading ratios.

To understand how the chemical bonding states of Fe/$Al_2O_3$ is affected by incorporating In into the catalyst, XPS measurements were performed over $Al_2O_3$ supported Fe, Fe20In (IE1), Fe10In (IE2), and Fe20In3 (IE3) catalysts after they achieved the steady state (see FIG. 9). The binding energy of C 1s peak at 284.6 eV was taken as a reference. In the case of pure Fe, the peaks at 711.5 and 725.1 eV are assigned to Fe 2p3/2 and Fe 2p1/2 of $Fe_2O_3$. Both Fe 2p peaks were shifted towards lower binding energy (710.5 eV for 2p3/2 and 724.1 eV for 2p1/2) when 5 mol % In (based on Fe) was incorporated into the catalyst. This shift could be attributed to electron transfer from Fe to In. Similar phenomenon was commonly encountered when incorporating the non-metal elements into metals. These two peaks did not move when further increasing the In composition up to 10% and 15% into the catalyst. However, new peaks at higher binding energies were found over these two catalysts. In the case of Fe10In (IE2), we found 712.35 and 725.95 eV for Fe2p3/2 and Fe2p1/2, respectively. The peaks were located at basically the same binding energies over Fe20In3 (IE3) (712.39 eV for Fe2p3/2 and 725.99 eV for Fe2p1/2). The modification of the chemical bonding state of Fe by In element appeared to affect the surface chemistry that could improve the olefin selectivity. It is noted that the peaks at 703 eV over Fe10In (IE2) and Fe20In3 (IE3) catalysts are related to In 3p1/2. This peak was less pronounced over Fe20In (IE1) due to the low In loading. It is also clear that the ratios of In/Fe peak area were systematically raised as In loading increased. This suggested that the In concentration near the surface layers can be increased when the In loading increased in the catalyst. This phenomenon was also observed in a range of bimetallic materials, intermetallic compounds, and transition metal ceramics.

Applicant discovered an efficient and selective catalyst composition for converting syngas to light olefins. Catalyst composition with from 85 mol % to 95 mol % iron metal and from 15 mol % to 5 mol % indium metal (mol % based on total moles of iron and indium) on alumina support exhibits high selectivity and superior stability with a moderate CO conversion in the reaction. Performance study shows systematic trends in CO conversion and selectivity as a function of Fe:In loading ratios. Detailed characterizations demonstrate an interaction between In and Fe and In composition is increased near the surface layers when In loading increases, which clearly affects the catalytic activity and selectivity in the FTS reaction. In addition, In element can improve the reducibility of the catalyst and also stabilize the surface-bounded CHx species that can promote C—C coupling towards olefins and inhibit $CH_4$ formation.

It is specifically intended that the present disclosure not be limited to the embodiments and illustrations contained herein, but include modified forms of those embodiments including portions of the embodiments and combinations of elements of different embodiments as come within the scope of the following claims.

The invention claimed is:

1. A catalyst comprising:
   a metallic catalytic composition consisting of:
   from 85 mol % to 95 mol % iron metal;
   from 15 mol % to 5 mol % indium metal, and
   a support impregnated with the metallic catalytic composition in a nanoparticle form, wherein the nanoparticle form of the metallic catalytic composition is defined by at least one iron salt and at least one indium salt having been introduced to the support then exposed to a reduction agent to reduce the iron salt and indium salt into the iron metal and the indium metal to form the catalytic composition on the support;
   wherein mol % is based on total moles of iron metal and indium metal.

2. The composition of claim 1 wherein the composition is void of a component selected from the group consisting of nitrogen, carbon, and combinations thereof.

3. The composition of claim 1 wherein the support component is alumina.

4. The composition of claim 3 consisting of
   from 9.7 wt % to 9.9 wt % iron metal;
   from 1 wt % to 3 wt % indium metal; and
   from 87.3 wt % to 89.1 wt % alumina.

5. The composition of claim 4 wherein the metallic catalytic composition consists of 90 mol % iron metal and 10 mol % indium metal, based on the total moles of iron and indium.

6. The catalyst composition of claim 4 wherein when the catalyst composition is contacted with a gaseous mixture comprising carbon monoxide, hydrogen and optionally water under reaction conditions, and the catalyst composition has
   from 40% to 60% light olefin selectivity,
   less than or equal to 20 wt % $CO_2$ selectivity, and
   less than or equal to 25 wt % methane selectivity.

7. The catalyst of claim 1, wherein a surface residence time of $CH_4$ on the catalyst composition is greater than 10 seconds.

8. A metallic catalytic composition consisting of:
   from 85 mol % to 95 mol % iron metal;
   from 15 mol % to 5 mol % indium metal,
   wherein mol % is based on total moles of iron metal and indium metal.

9. A catalyst consisting of:
   a metallic catalytic composition consisting of:
   from 85 mol % to 95 mol % iron metal;
   from 15 mol % to 5 mol % indium metal, and
   having a support impregnated with at least one iron salt and at least one indium salt and exposed to a mixture of $H_2/N_2$ gas to provide the iron metal and the indium metal on the support;
   wherein mol % is based on total moles of iron metal and indium metal.

10. A catalyst consisting essentially of:
    a metallic catalytic composition consisting of:
    from 85 mol % to 95 mol % iron metal;
    from 15 mol % to 5 mol % indium metal, and
    having a support impregnated with at least one iron salt and at least one indium salt and exposed to a mixture of $H_2/N_2$ gas to provide the iron metal and the indium metal on the support;
    wherein mol % is based on total moles of iron metal and indium metal, and
    wherein the support is a mixture of delta phase and gamma phase alumina.

11. A metallic catalytic composition consisting of:
    9 wt % iron;
    1 wt % indium, and
    89.1 wt % alumina.

12. A metallic catalytic composition consisting of:
    8 wt % iron;
    2 wt % indium, and
    88.2 wt % alumina.

13. A metallic catalytic composition consisting of:
    7 wt % iron;
    3 wt % indium, and
    87.3 wt % alumina.

14. A process comprising:
    contacting, under reaction conditions, a gaseous mixture comprising carbon monoxide, hydrogen and optionally water with the catalyst composition of claim 1 comprising
    forming a reaction product comprising light olefins wherein the reaction conditions comprise a tubular reactor at a reaction temperature from 150° C. to 450° C., a pressure from 1 bar to 6 bar and a $H_2$:CO ratio from 1-3:1.

15. The process of claim 14 comprising
    exposing, before the contacting, the catalyst composition to a mixture of $H_2/N_2$ gas at a temperature from 350° C. to 450° C.; and
    reducing the iron and indium.

16. The process of claim 14 comprising forming a reaction product comprising
    from 40 wt % to 60 wt % light olefin,
    less than or equal to 20 wt % $CO_2$, and
    less than or equal to 25 wt % methane.

* * * * *

UNITED STATES PATENT AND TRADEMARK OFFICE
CERTIFICATE OF CORRECTION

PATENT NO. : 12,179,179 B2
APPLICATION NO. : 17/691082
DATED : December 31, 2024
INVENTOR(S) : John Kuhn et al.

Page 1 of 1

It is certified that error appears in the above-identified patent and that said Letters Patent is hereby corrected as shown below:

In the Claims

Column 14, Claim 11, Line 33, "9 wt" should be --9.9 wt--.

Column 14, Claim 12, Line 37, "8 wt" should be --9.8 wt--.

Column 14, Claim 13, Line 41, "7 wt" should be --9.7 wt--.

Column 14, Claim 14, Lines 47-48, "comprising" should be --comprising; and--.

Signed and Sealed this
Eighth Day of April, 2025

Coke Morgan Stewart
*Acting Director of the United States Patent and Trademark Office*